United States Patent [19]
Akiba et al.

[11] Patent Number: 5,780,669
[45] Date of Patent: Jul. 14, 1998

[54] SELECTIVE DEHALOGENATION PROCESS

[75] Inventors: Toshifumi Akiba; Takanobu Ikeya; Hirofumi Kawanishi; Yusuke Yukimoto; Shinji Kamihara; Tsutomu Ebata, all of Tokyo, Japan

[73] Assignee: Daiichi Pharmaceutical Co., Ltd., Tokyo, Japan

[21] Appl. No.: 592,402

[22] PCT Filed: Aug. 3, 1994

[86] PCT No.: PCT/JP94/01280

§ 371 Date: Feb. 1, 1996

§ 102(e) Date: Feb. 1, 1996

[87] PCT Pub. No.: WO95/04712

PCT Pub. Date: Feb. 16, 1995

[30] Foreign Application Priority Data

Aug. 5, 1993 [JP] Japan ................... 5-194423

[51] Int. Cl.$^6$ ................... C07C 69/74
[52] U.S. Cl. ................... 560/124; 562/506
[58] Field of Search ................... 562/506; 560/124

[56] References Cited

PUBLICATIONS

Gassen, Journal of Fluorine Chemistry, vol. 49, pp. 127–139, 1990.

*Primary Examiner*—Michael L. Shippen
*Attorney, Agent, or Firm*—Sughrue, Mion, Zinn, Macpeak & Seas, PLLC

[57] ABSTRACT

A compound represented by the following formula (1) or (3):

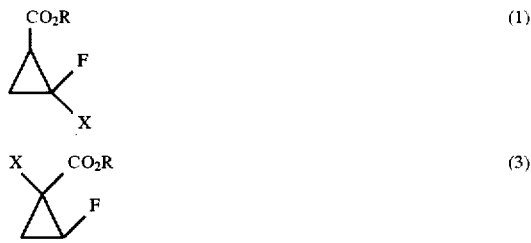

is subjected to a catalytic hydrogenolysis reaction in the presence of a base and thus a compound represented by the following formula (2):

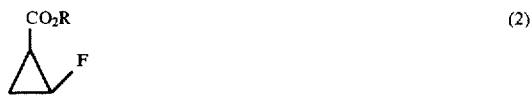

wherein R represents a hydrogen atom or an alkyl group having 1 to 4 carbon atoms and X represents a chlorine atom or a bromine atom;

is easily produced. This compound is usable as an intermediate for the preparation of drugs.

9 Claims, No Drawings

SELECTIVE DEHALOGENATION PROCESS

TECHNICAL FIELD

This invention relates to a novel process for producing a starting compound to be used in the preparation of a quinolone derivative (refer to JP-A-2-231475, the term "JP-A" as used herein means an "unexamined published Japanese patent application") which is expected as an excellent antimicrobial agent.

BACKGROUND ART 1,2-cis-2-Fluorocyclopropanecarboxylic acid, which means a compound wherein a carboxylate substituent and a fluorine atom are located on the same side of the cyclopropane ring plane, represented by the following structural formula

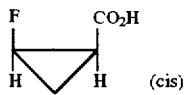

has been produced by the process described below. Namely, bromofluorocarbene is added to butadiene to thereby give 1-bromo-1-fluoro-2-vinylcyclopropane. Next, this compound is converted into a carboxylic acid compound by oxidizing its vinyl group. Further, the carboxylic acid compound is esterified followed by debromination. After separating 1,2-cis-2-fluorocyclopropanecarboxylate of the cis-configuration from the compound of the trans-configuration, the ester is hydrolyzed into carboxylic acid [refer to Bulletin of Faculty of Education, Wakayama University, 33, 33 (1984)].

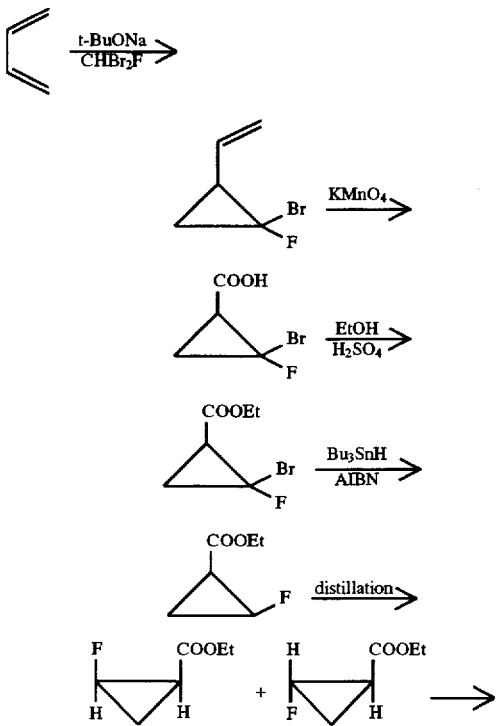

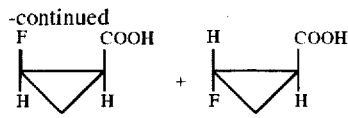

However, the above-mentioned process requires a number of reaction steps. In addition, tributyltin hydride ($Bu_3SnH$), which is toxic and expensive, is used in the step of debromination. These problems inevitably make this process disadvantageous from an industrial viewpoint.

On the other hand, there has been reported a process for the dechlorination of 2-chloro-2-fluorocyclopropanecarboxylic acid through a catalytic hydrogenolysis reaction in the presence of a base. By this process, however, no 2-fluorocyclopropanecarboxylic acid of the cis-configuration but 2-fluorocyclopropanecarboxylic acid of the trans-configuration alone can be obtained at a low yield [refer to Journal of Fluorine Chemistry, 49, 127 (1990)].

It is an object of the present invention to provide a process whereby a 2-fluorocyclopropanecarboxylic acid derivative, in particular, 1,2-cis-2-fluorocyclopropanecarboxylic acid derivative can be produced safely, economically and advantageously from an industrial viewpoint.

DISCLOSURE OF THE INVENTION

Under these circumstances, the present inventors have conducted extensive studies. As a result, they have found out that when a compound represented by the following formula (1) (hereinafter, referred to as the compound (1) and the same will apply to other compounds represented by numbered formulae hereinafter) is subjected to a catalytic hydrogenolysis reaction in the presence of a base under mild conditions, dehalogenation unexpectedly proceeds with retention of the configuration and thus a 1,2-cis-2-fluorocyclopropanecarboxylic acid derivative can be obtained at a high yield. They have further found out that when the compound (3) as will be shown hereinafter is treated under the same conditions, dehalogenation proceeds similarly, thus completing the present invention.

Accordingly, the present invention relates to a process for producing a compound represented by the following formula (2):

wherein R represents a hydrogen atom or an alkyl group having 1 to 4 carbon atoms; which comprises subjecting a compound represented by the following formula (1):

wherein R is as defined above; and X represents a chlorine or bromine atom; to a catalytic hydrogenolysis reaction in the presence of a base.

The present invention further relates to a process for producing a compound represented by the following formula (2):

(2)

wherein R represents a hydrogen atom or an alkyl group having 1 to 4 carbon atoms; which comprises subjecting a compound represented by the following formula (3):

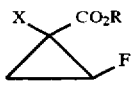

(3)

wherein R is as defined above; and X represents a chlorine or bromine atom; to a catalytic hydrogenolysis reaction in the presence of a base.

The present invention furthermore relates to a process for producing the compound (2) which comprises treating the compound (1) or the compound (3) in the presence of 1,2-diaminoethane with the use of a catalyst selected from Raney nickel and palladium/carbon under a hydrogen gas atmosphere of a hydrogen gas pressure ranging from 1 to 50 atm.

The present invention further relates to the above-mentioned processes in which the compound of the formula (2) is a 1,2-cis-compound wherein a —$CO_2R$ substituent and a fluorine atom are located on the same side of the cyclopropane ring.

The present invention furthermore relates to the above-mentioned processes wherein the catalytic hydrogenolysis reaction proceeds with retention of the configuration.

The present invention relates to the above-mentioned processes wherein the treatment comprises a reaction which proceeds with retention of the configuration.

The term "catalytic hydrogenolysis reaction" as used herein means a reaction for converting a chlorine atom or a bromine atom, which is a substituent of the compound (1) or the compound (3), into a hydrogen atom by treating the reaction substrate in a solution in the presence of a catalyst selected from among various metal catalysts under a hydrogen gas atmosphere.

The compound (1) to be used in the process of the present invention can be obtained by, for example, the following method. That is, a compound represented by the formula (4):

(4)

wherein X represents a chlorine atom or a bromine atom; is reacted with a compound represented by the formula (5):

(5)

wherein R represents a hydrogen atom or an alkyl group having 1 to 4 carbon atoms; in the presence of a catalyst such as rhodium.

On the other hand, the compound (3) can be obtained by the following method. That is, a compound represented by the formula (6):

(6)

wherein R' represents a hydrogen atom or an alkyl group having 1 to 4 carbon atoms; is reacted with a dihalogenoacetic acid ester in the presence of a base in accordance with, for example, the method of L. McCoy [J. Am. Chem.. Soc., 80, 6568 (1958)] to thereby give a compound represented by the formula (7):

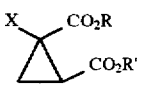

(7)

wherein R and R' independently represent each an alkyl group having 1 to 4 carbon atoms. Then one of the ester groups of the compound (7) is hydrolyzed in a conventional manner to thereby give a compound represented by the formula (8):

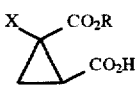

(8)

wherein R represents an alkyl group having 1 to 4 carbon atoms; followed by the treatment of the compound (8) with a fluorine gas in the presence of a base.

In the compounds (1), (2) and (3), when R is a hydrogen atom, then the —$CO_2R$ substituent is a carboxyl group, and when R is an alkyl group, then the —$CO_2R$ substituent is an alkoxycarbonyl group. As examples of the alkoxycarbonyl group, methoxycarbonyl, ethoxycarbonyl, isopropoxycarbonyl, n-butoxycarbonyl, iso-butoxycarbonyl and tert-butoxycarbonyl groups may be included.

In the compounds (1) and (3), the halogen represented by X is a chlorine atom or a bromine atom.

As the catalyst to be used in the process according to the present invention, metal catalysts which are commonly used in catalytic hydrogenolysis reactions may be used. Among these catalysts, palladium catalysts such as palladium/carbon or palladium black and Raney nickel may be used as preferable examples thereof.

In the present invention, the catalytic hydrogenolysis reaction is performed in the presence of a base. As the base to be used herein, either an inorganic base or an organic base may be selected. Examples of the inorganic base include alkali metal hydroxides such as sodium hydroxide, potassium hydroxide or lithium hydroxide and alkali metal carbonates such as potassium carbonate. On the other hand, examples of the organic base include alkylamines such as methylamine, ethylamine, diethylamine or triethylamine, alkanolamines such as ethanolamine, alkylenediamines such as 1,2-diaminoethane, trimethylenediamine or hexamethylenediamine, aralkylamines such as benzylamine, dicyanediamide and saturated or aromatic heterocyclic compounds such as pyridine or piperidine. Among these bases, organic bases are preferable and 1,2-diaminoethane is particularly preferable.

In the process of the present invention, the starting compound is usually used in a state of a solution. The diluent or solvent to be used herein is not limited, so long as it remains inert throughout the reaction. As examples thereof, alcohols such as methanol, ethanol, isopropanol or tert-butyl alcohol, ethers such as diethyl ether, diisopropyl ether, 1,4-dioxane or tetrahydrofuran, hydrocarbons such as toluene, hexane or cyclohexane and water may be included. These substances may be used as a solvent either individually or in combination of two or more thereof.

The process of the present invention is performed under a hydrogen gas atmosphere. The hydrogen pressure is selected from a range of 1 to 100 atm (bar). It is preferable to perform the process of the present invention under a hydrogen pressure selected from a range of 1 to 50 atm (bar).

The process of the present invention is performed at a temperature selected usually from a range of 0° to 80° C., preferably from 5° to 50° C.

To effect the process of the present invention, the base is used at a ratio of from 0.55 to 11 mol (including a portion of the base required for the elimination of an acid component formed with the progress of the reaction) per mol of the compound (1) or the compound (3). In the presence of a necessary and sufficient amount of a catalyst, the hydrogenolysis reaction is carried out under an atmospheric or elevated hydrogen gas atmosphere at the temperature as specified above over several hours to several ten hours. When these reaction conditions are appropriately combined together, the compound (2) can be obtained at a high yield with retention of the configuration of the compound (1). Similarly, the compound (2) can be obtained from the compound (3) too.

To effect the process of the present invention, the reaction conditions are selected in such a manner as "to establish milder conditions as a whole from various conditions as specified above". For example, when a high reaction temperature is employed, then the hydrogen gas pressure may be regulated to a low level. When a high hydrogen gas pressure is employed, on the contrary, then a low reaction temperature may be used. When the reaction temperature and the hydrogen gas pressure are both high, then the reaction time is shortened.

The 1,2-cis-2-fluorocyclopropanecarboxylic acid derivative and the 1,2-trans-2-fluorocyclopropanecarboxylic acid derivative obtained by the process of the present invention can be easily separated from each other by a conventional separation method. In the case of the compound represented by the general formula (2) wherein R is an ethyl group, for example, the separation can be easily made through distillation under reduced pressure, as will be shown in the following examples.

When the 1,2-cis-2-fluorocyclopropanecarboxylic acid derivative thus obtained is an ester, it can be derived into a 1,2-cis-2-fluorocyclopropanecarboxylic acid by a conventional hydrolysis reaction with the use of an acid or a base, or a conventional catalytic hydrogenolysis reaction. This hydrolysis is effected by, for example, treating the derivative in a mixture of a mineral acid such as hydrochloric acid with an alcohol or in a mixture of an aqueous solution of an alkali hydroxide such as sodium hydroxide with an alcohol. The 1,2-cis-2-fluorocyclopropanecarboxylic acid can be derived into a quinolone derivative, which is an excellent antimicrobial agent, in accordance with the method disclosed by JP-A-2-231475.

BEST MODE FOR CARRYING OUT THE INVENTION

To further illustrate the present invention in greater detail, the following Examples and Referential Examples will be given. However, it is to be understood that the present invention is not restricted thereto. In these Examples, compounds specified as cis- or trans-compounds are those the configurations of which are determined depending on the locations of a carboxylate substituent and a fluorine atom. That is to say, a compound wherein a carboxylate substituent and a fluorine atom are located at the same side of the cyclopropane ring is referred to as a cis-compound, while a compound wherein these groups are located at different sides is referred to as a trans-compound.

[REFERENTIAL EXAMPLE 1]

Ethyl 2-chloro-2-fluoro-1-cyclopropanecarboxylate 16.9 mg of tetrakis(triphenylacetato) dirhodium was added to 10 ml of dichloromethane and dissolved therein. Then 370 mg of powdery Molecular Sieves 4A was added thereto. The reaction container was soaked in a dry ice/acetone bath and 1.0 g of 1-chloro-1-fluoroethylene was dissolved in the mixture. While maintaining the temperature of this solution at $-35°$ C. to $-40°$ C., 5.3 ml of a solution of 2.5 mmol of ethyl diazoacetate in dichloromethane was dropped thereinto under an argon gas atmosphere. The addition was made in such a manner that a half of the solution was dropped within 15 minutes and another half was dropped within 30 minutes. After the completion of the addition, the reaction mixture was slowly returned to room temperature. When analyzed by gas chromatography, it was found out that the reaction conversion ratio was 100%, the yield was 91% and the ratio of cis:trans was 1.59:1.0. The analytical data of the title product are as follows.

b.p.: $60°–56°$ C./20–24 mmHg.

$^1$H-NMR (CDCl$_3$):

cis-compound:

δ: 1.30 (3H, t, J=7.3 Hz), 1.69 (1H, td, J=7.3, 9.3 Hz), 2.24 (1H, td, J=7.8, 16.1 Hz), 2.38 (1H, ddd, J=1.0, 7.8, 10.0 Hz), 4.22 (2H, q, J=7.3 Hz).

trans-compound:

δ: 1.31 (3H, t, J=7.3 Hz), 1.83–1.94 (2H, m), 2.54 (1H, m), 4.23 (2H, q, J=7.3 Hz).

[REFERENTIAL EXAMPLE 2]

Methyl 2-tert-butoxycarbonyl-1-chloro-1-cyclopropanecarboxylate 80 g of 60% sodium hydride was suspended in 1,000 ml of N,N-dimethylformamide. To this suspension was dropped 352 ml of tert-butyl acrylate within 30 minutes under ice-cooling. Then 207 ml of methyl dichloroacetate was dropped into this reaction mixture within 1.5 hours while maintaining the internal temperature at 10° C. After the completion of the addition, the mixture was stirred for 2 hours while maintaining the internal temperature at 10° to 20° C. Then the reaction mixture was neutralized by adding concentrated hydrochloric acid and water was further added thereto. The reaction mixture was extracted with ethyl acetate and the organic layer was washed with a saturated aqueous solution of sodium chloride. The extract was dried over anhydrous sodium sulfate and then the solvent was evaporated under reduced pressure. The obtained residue was distilled under reduced pressure to thereby give 384 g (yield 84%) of methyl 2-tert-butoxycarbonyl-1-chloro-1-cyclopropanecarboxylate in the form of a colorless oily product.

b.p.: $96°–105°$ C./1 mmHg.

$^1$H-NMR (CDCl$_3$):

δ: 1.44 and 1.49 (9H, each s), 1.61 (3/5H, dd, J=6.8, 9.8 Hz), 1.88 (1H, d, J=8.8 Hz), 2.10 (2/5H, dd, J=6.3, 7.8 Hz), 2.37 (2/5H, dd, J=7.8, 9.8 Hz), 2.60 (3/5H, dd, J=8.8, 8.8 Hz), 3.78 and 3.81 (3H, each s).

[REFERENTIAL EXAMPLE 3]

2-Chloro-2-methoxycarbonyl-1-cyclopropanecarboxylic acid 158 g of methyl 2-tert-butoxycarbonyl-1-chloro-1-cyclopropanecarboxylate was dissolved in 350 ml of dichloromethane. Then 160 ml of trifluoroacetic acid was added thereto and the obtained mixture was stirred at room temperature for 6 hours. The reaction mixture was concentrated under reduced pressure and n-hexane was added to the residue. The crystals thus formed were collected by filtration and washed with n-hexane. Thus 116 g (yield 97%) of 2-chloro-2-methoxycarbonyl-1-cyclopropanecarboxylic acid was obtained as colorless crystals.

m.p.: $77.7°–79.1°$ C.

$^1$H-NMR (CDCl$_3$):

δ: 1.76 (2/5H, dd, J=6.8, 9.8 Hz), 1.95 (3/5H, dd, J=6.3, 7.8 Hz), 2.01 (3/5H, dd, J=5.8, 9.4 Hz), 2.20 (2/5H, dd, J=6.8, 7.8 Hz), 2.47 (2/5H, dd, J=7.8, 9.8 Hz), 2.72 (3/5H, dd, J=7.8, 9.3 Hz), 3.79 and 3.83 (3H, each s).

[REFERENTIAL EXAMPLE 4]

Methyl 1-chloro-2-fluoro-1-cyclopropanecarboxylate

To 111 g of 2-chloro-2-methoxycarbonyl-1-cyclopropanecarboxylic acid was added 200 ml of water. Further, a solution of 24.87 g of sodium hydroxide dissolved in 300 ml of water was added thereto under ice-cooling and stirring to thereby give sodium salt. To this aqueous solution was added 52.25 g of sodium fluoride. Next, 1.3 equivalents, to carboxylic acid, of 10% (v/v) fluorine gas (diluted with nitrogen: 600 ml/min) was bubbled into this solution under ice-cooling and stirring. After the completion of the bubbling, the pH value of the reaction mixture was regulated to 8 to 9 by adding a 1N aqueous solution of sodium hydroxide. Then it was extracted with two 250 ml portions of dichloromethane. The organic layer was collected and dried over sodium sulfate. After evaporating the solvent under reduced pressure, 75 g of the title compound was obtained in the form of a crude product (cis:trans=3:2). After adjusting pH value of the separated aqueous layer to 2 to 3 with hydrochloric acid, it was extracted with two 100 ml portions of dichloromethane. Thus 23.1 g of the starting compound was recovered. After distilling the crude reaction product, the total yield of the cis- and trans-compounds was 76.4% (calculated by excluding the recovered starting compound). The analytical data of the title compound are as follows.

b.p.:
  cis-compound: 79°–81° C./40 mmHg.
  trans-compound: 83°–85° C./40 mmHg.

$^1$H-NMR (CDCl$_3$):
  cis-compound:
    δ: 1.63 (1H, ddd, J=12.2, 8.8, 6.8 Hz), 2.46 (1H, ddd, J=23.4, 8.8, 4.9 Hz), 3.85 (3H, s), 4.88 (1H, ddd, J=63.0, 6.8, 4.9 Hz).
  trans-compound:
    δ: 1.69 (1H, ddd, J=21.5, 8.3, 4.4 Hz), 1.98 (1H, ddd, J=16.6, 8.3, 6.8 Hz), 3.80 (3H, s), 4.88 (1H, ddd, J=64.5, 6.8, 4.4 Hz).

EXAMPLE 1

Ethyl 2-fluoro-1-cyclopropanecarboxylate

An internal glass tube was introduced into an autoclave and 0.5 g of ethyl 2-chloro-2-fluoro-1-cyclopropanecarboxylate (cis:trans=1.4:1), 0.5 ml of Raney nickel and 5 ml of ethanol were fed thereinto. Then 0.54 g of 1,2-diaminoethane was further added and the mixture was stirred at room temperature under an elevated hydrogen gas atmosphere (50 kgf/cm$^2$) for 24 hours. After the completion of the reaction, the catalyst was filtered off. Then the reaction mixture was analyzed by gas chromatography. As a result, it was found out that the reaction conversion rate was 100%, the yield was 88.9% and the cis:trans ratio was 1.4:1. The analytical data of the title compound are as follows.

b.p.:
  cis-compound: 76.5°–77° C./30 mmHg.
  trans-compound: 63°–64° C./50 mmHg.

$^1$H-NMR (CDCl$_3$):
  cis-compound:
    δ: 1.11–1.18 (1H, m), 1.29 (3H, t, J=7.1 Hz), 1.75–1.84 (2H, m), 4.20 (2H, q, J=7.1 Hz), 4.73 (1H, dm, J=65.1 Hz).
  trans-compound:
    δ: 1.24–1.34 (1H, m), 1.27 (3H, t, J=7.1 Hz), 1.41–1.49 (1H, m), 2.04–2.11 (1H, m), 4.14 (2H, q, J=7.1 Hz), 4.80 (1H, dm, J=63.5 Hz).

EXAMPLE 2

2-Fluoro-1-cyclopropanecarboxylic acid

An internal glass tube was introduced into an autoclave and 1.0 g of 2-chloro-2-fluoro-1-cyclopropanecarboxylic acid (cis:trans=1.2:1), 1.0 ml of Raney nickel and 10 ml of ethanol were fed thereinto. Then 4.34 g of 1,2-diaminoethane was further added and the mixture was stirred at 50° C. under an elevated hydrogen gas atmosphere (10 kgf/cm$^2$) for 24 hours. After the completion of the reaction, the catalyst was filtered off. Then the reaction mixture was analyzed by gas chromatography. As a result, it was found out that the reaction conversion rate was 100%, the yield was 91% and the cis:trans ratio was 1.2:1. The analytical data of the title compound are as follows.

m.p.:
  cis-compound: 73°–74° C.
  trans-compound: 46°–48° C.

$^1$H-NMR (CDCl$_3$):
  cis-compound:
    δ: 1.18–1.29 (1H, m), 1.78–1.89 (2H, m), 4.80 (1H, dm, J=64.5 Hz), 10.26 (1H, b).
  trans-compound:
    δ: 1.31–1.42 (1H, m), 1.49–1.60 (1H, m) 2.04–2.13 (1H, m), 4.85 (1H, dm, J=63.5 Hz), 10.20 (1H, b).

EXAMPLE 3

Ethyl 2-fluoro-1-cyclopropanecarboxylate

An internal glass tube was introduced into an autoclave and 211 mg of ethyl 2-bromo-2-fluoro-1-cyclopropanecarboxylate [obtained in accordance with the method of Bulletin of Faculty of Education, Wakayama University, 33, 33 (1984); cis:trans=0.8:1], 40 mg of 5% palladium-carbon (moisture content: 55% wet) and 8 ml of ethanol were fed thereinto. Then 90 mg of 1,2-diaminoethane was further added and the mixture was stirred at room temperature under an elevated hydrogen gas atmosphere (50 kgf/cm$^2$) for 48 hours. After the completion of the reaction, the catalyst was filtered off. Then the reaction mixture containing the title compound was analyzed by gas chromatography. As a result, it was found out that the reaction conversion rate was 95%, the yield was 81% and the cis:trans ratio was 0.8:1.

EXAMPLE 4

Ethyl 2-fluoro-1-cyclopropanecarboxylate

An internal glass tube was introduced into an autoclave and 0.5 g of ethyl 2-bromo-2-fluoro-1-cyclopropanecarboxylate (cis:trans=0.8:1), 0.5 ml of Raney nickel and 5 ml of ethanol were fed thereinto. Then 0.43 g of 1,2-diaminoethane was further added and the mixture was stirred at room temperature under a hydrogen gas atmosphere (1 kgf/cm$^2$) for 24 hours. After the completion of the reaction, the catalyst was filtered off. Then the reaction mixture containing the title compound was analyzed by gas chromatography. As a result, it was found out that the reaction conversion rate was 100%, the yield was 78% and the cis:trans ratio was 0.8:1.

EXAMPLE 5

2-Fluoro-1-cyclopropanecarboxylic acid

An internal glass tube was introduced into an autoclave and 183 mg of 2-bromo-2-fluoro-1-cyclopropanecarboxylic acid (cis:trans=0.8:1), 20 mg of 5% palladium-carbon (55% wet) and 1.8 ml of ethanol were fed thereinto. Then 130 mg of 1,2-diaminoethane was further added and the mixture was stirred at room temperature under an elevated hydrogen gas atmosphere (50 kgf/cm$^2$) for 24 hours. After the completion of the reaction, the catalyst was filtered off. Then the reaction mixture containing the title compound was analyzed by gas chromatography. As a result, it was found out that the reaction conversion rate was 100%, the yield was 73% and the cis:trans ratio was 0.8:1.

EXAMPLE 6
2-Fluoro-1-cyclopropanecarboxylic acid

An internal glass tube was introduced into an autoclave and 0.5 g of ethyl 2-bromo-2-fluoro-1-cyclopropanecarboxylic acid (cis:trans=0.8:1), 0.5 ml of Raney nickel and 5 ml of ethanol were fed thereinto. Then 0.49 g of 1,2-diaminoethane was further added and the mixture was stirred at room temperature under a hydrogen gas atmosphere (1 kgf/cm$^2$) for 24 hours. After the completion of the reaction, the catalyst was filtered off. Then the reaction mixture containing the title compound was analyzed by gas chromatography. As a result, it was found out that the reaction conversion rate was 100%, the yield was 86% and the cis:trans ratio was 0.8:1.

EXAMPLE 7
Ethyl 2-fluoro-1-cyclopropanecarboxylate

An internal glass tube was introduced into an autoclave and 0.5 g of ethyl 1-chloro-2-fluoro-1-cyclopropanecarboxylate (cis:trans=1.4:1), 0.5 ml of Raney nickel and 5 ml of ethanol were fed thereinto. Then 0.18 mg of 1,2-diaminoethane was further added and the mixture was stirred at room temperature under an elevated hydrogen gas atmosphere (10 kgf/cm$^2$) for 48 hours. After the completion of the reaction, the catalyst was filtered off. Then the reaction mixture containing the title compound was analyzed by gas chromatography. As a result, it was found out that the reaction conversion rate was 95%, the yield was 81% and the cis:trans ratio was 0.3:1.

EXAMPLE 8
2-Fluoro-1-cyclopropanecarboxylic acid

An internal glass tube was introduced into an autoclave and 0.5 g of 1-chloro-2-fluoro-1-cyclopropanecarboxylic acid (cis:trans=0.8:1), 0.5 ml of Raney nickel and 5 ml of ethanol were fed thereinto. Then 2.17 g of 1,2-diaminoethane was further added and the mixture was stirred at room temperature under an elevated hydrogen gas atmosphere (10 kgf/cm$^2$) for 24 hours. After the completion of the reaction, the catalyst was filtered off. Then the reaction mixture containing the title compound was analyzed by gas chromatography. As a result, it was found out that the reaction conversion rate was 100%, the yield was 57% and the cis:trans ratio was 0.1:1.

The analytical conditions of the gas chromatography employed in the above Referential Example 1 and Examples 1, 3, 4 and 7 are as follows.

Column: TC-WAX (GL Sciences) 30 m×0.25 mm in diameter.
Column. temp.: 70° C.
Injector temp.: 200° C.
Detector temp.: 200° C.
Carrier gas: helium.
Retention time:
Ethyl 2-chloro-2-fluoro-1-cyclopropanecarboxylate
 cis-compound: 6.7 minutes.
 trans-compound: 6.2 minutes.
Ethyl 2-bromo-2-fluoro-1-cyclopropanecarboxylate
 cis-compound: 13.9 minutes.
 trans-compound: 12.7 minutes.
Ethyl 1-chloro-2-fluoro-1-cyclopropanecarboxylate
 cis-compound: 9.4 minutes.
 trans-compound: 10.9 minutes.
Ethyl 2-fluoro-1-cyclopropanecarboxylate
 cis-compound: 8.5 minutes.
 trans-compound: 2.7 minutes.

The analytical conditions of the gas chromatography employed in the above Examples 2, 5, 6 and 8 are as follows.

Column: Unisole F-200 (GL Sciences) 6 FT×2 mm in diameter.
Column. temp.: 140° C.
Injector temp.: 200° C.
Detector temp.: 200° C.
Carrier gas: nitrogen.
Retention time:
2-Chloro-2-fluoro-1-cyclopropanecarboxylic acid
 both of cis- and trans compounds: 12.5 minutes.
2-Bromo-2-fluoro-1-cyclopropanecarboxylic acid
 cis-compound: 7.0 minutes.
 trans-compound: 4.5 minutes.
1-Chloro-2-fluoro-1-cyclopropanecarboxylic acid
 both of cis- and trans-compounds: 12.4 minutes.
2-Fluoro-1-cyclopropanecarboxylic acid
 cis-compound: 8.5 minutes.
 trans-compound: 2.7 minutes.

Industrial Applicability:

By using the process of the present invention, a 1,2-cis-2-fluorocyclopropanecarboxylic acid derivative, which is useful as a starting material for the preparation of a quinolone derivative being excellent as an antimicrobial agent, can be industrially and advantageously produced.

We claim:

1. A process for producing a compound represented by the following formula (2):

wherein R represents a hydrogen atom or an alkyl group having 1 to 4 carbon atoms;

which comprises subjecting a compound represented by the following formula (1):

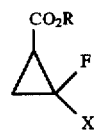

wherein R is as defined above; and X represents a chlorine or bromine atom;

to a catalytic hydrogenolysis reaction in the presence of a base, wherein the reaction proceeds with a retention of steroconfiguration of the compound represented by the formula (2) reacted in the compound represented by the formula (1) produced.

2. A process for producing a compound represented by the following formula (2):

wherein R represents a hydrogen atom or an alkyl group having 1 to 4 carbon atoms;

which comprises subjecting a compound represented by the following formula (3):

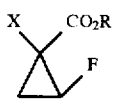 (3)

wherein R is as defined above; and X represents a chlorine or bromine atom;
to a catalytic hydrogenolysis reaction in the presence of a base, wherein the reaction proceeds with a retention of stereoconfiguration of the compound represented by the formula (3) reacted in the compound represented by the formula (2) produced.

3. A process for producing a compound represented by the following formula (2):

 (2)

wherein R represents a hydrogen atom or an alkyl group having 1 to 4 carbon atoms;
which comprises treating a compound represented by the following formula (1):

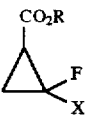 (1)

wherein R is as defined above; and X represents a chlorine or bromine atom;
in the presence of a base and a metal catalyst under a hydrogen gas atmosphere, wherein the reaction proceeds with a retention of stereoconfiguration of the compound represented by the formula (2) reacted in the compound represented by the formula (1) produced.

4. A process as claimed in claim 3, wherein said metal catalyst is Raney nickel or palladium/carbon.

5. A process as claimed in claim 4, wherein said base is 1,2-diaminoethane.

6. A process as claimed in claim 5, wherein the compound of the formula (2) is a 1,2-cis-compound having a —CO₂R substituent and a fluorine atom which are located in the same side of the cyclopropane ring.

7. A process for producing a compound represented by the following formula (2):

 (2)

wherein R represents a hydrogen atom or an alkyl group having 1 to 4 carbon atoms;

which comprises subjecting a compound represented by the following formula (1):

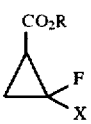 (1)

wherein R is as defined above; and X represents a chlorine or bromine atom;

in the presence of 1,2-diaminoethane with the use of Raney nickel or palladium-carbon as a catalyst under a hydrogen gas atmosphere of a hydrogen gas pressure within a range of 1 to 50 atm., wherein the reaction proceeds with a retention of stereoconfiguration of the compound represented by the formula (2) reacted in the compound represented by the formula (1) produced.

8. A process as claimed in claim 7, wherein the compound of the formula (2) is a 1,2-cis-compound having a —CO₂R substituent and a fluorine atom which are located in the same side of the cyclopropane ring.

9. A process for producing a compound represented by the following formula (2):

 (2)

wherein R represents a hydrogen atom or an alkyl group having 1 to 4 carbon atoms;

which comprises treating a compound represented by the following formula (3):

 (3)

wherein R is as defined above; and X represents a chlorine or bromine atom;

in the presence of 1,2-diaminoethane with the use of Raney nickel or palladium-carbon as a catalyst under a hydrogen gas atmosphere of a hydrogen gas pressure within a range of 1 to 50 atm., wherein the reaction proceeds with a retention of the stereoconfiguration of the compound represented by the formula (2) in the compound represented by the formula (1) produced.

* * * * *